United States Patent
Marks et al.

(10) Patent No.: US 7,147,601 B2
(45) Date of Patent: Dec. 12, 2006

(54) SIGNAL AVERAGING USING GATING SIGNAL OBTAINED FROM AUTOCORRELATION OF INPUT SIGNALS

(75) Inventors: Lloyd Marks, Westfield, NJ (US); Michael Smith, Oradell, NJ (US)

(73) Assignee: Smithmarks, Inc., Ridgefiled, NJ (US)

( * ) Notice: Subject to any disclaimer, the term of this patent is extended or adjusted under 35 U.S.C. 154(b) by 590 days.

(21) Appl. No.: 10/673,328

(22) Filed: Sep. 30, 2003

(65) Prior Publication Data
US 2005/0070808 A1    Mar. 31, 2005

(51) Int. Cl.
*A61B 5/02*    (2006.01)
(52) U.S. Cl. .................................. 600/500; 600/504
(58) Field of Classification Search ............. 600/485, 600/480, 500–503, 504
See application file for complete search history.

(56) References Cited

U.S. PATENT DOCUMENTS 4,548,211 A * 10/1985 Marks ........................ 600/507
5,558,096 A *  9/1996 Palatnik ..................... 600/500

* cited by examiner

*Primary Examiner*—Charles A Marmor, II
*Assistant Examiner*—Zoe Baxter
(74) *Attorney, Agent, or Firm*—Blank Rome LLP

(57) ABSTRACT

A plethysmographic or other signal is autocorrelated to give a first-pass determination of the distances among individual waveforms. A waveform is isolated, tested to determine whether its amplitude remains in suitable bounds for signal averaging, and convolved with the signal to match it with the other waveforms for averaging. Thus, a separate gating signal is not needed for signal averaging.

22 Claims, 3 Drawing Sheets

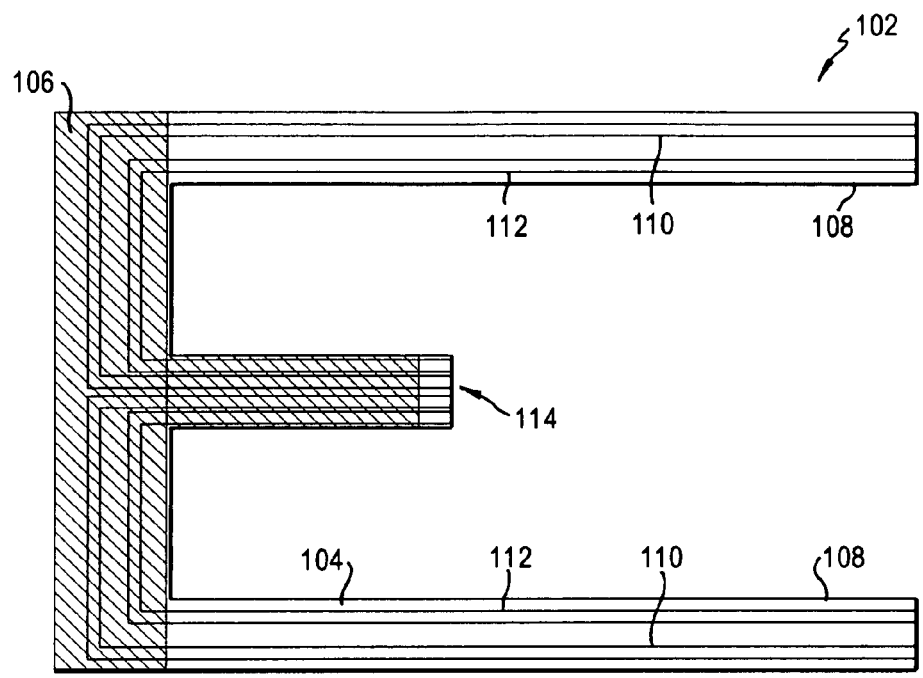
FIG. 1 (PRIOR ART)
FIG. 2
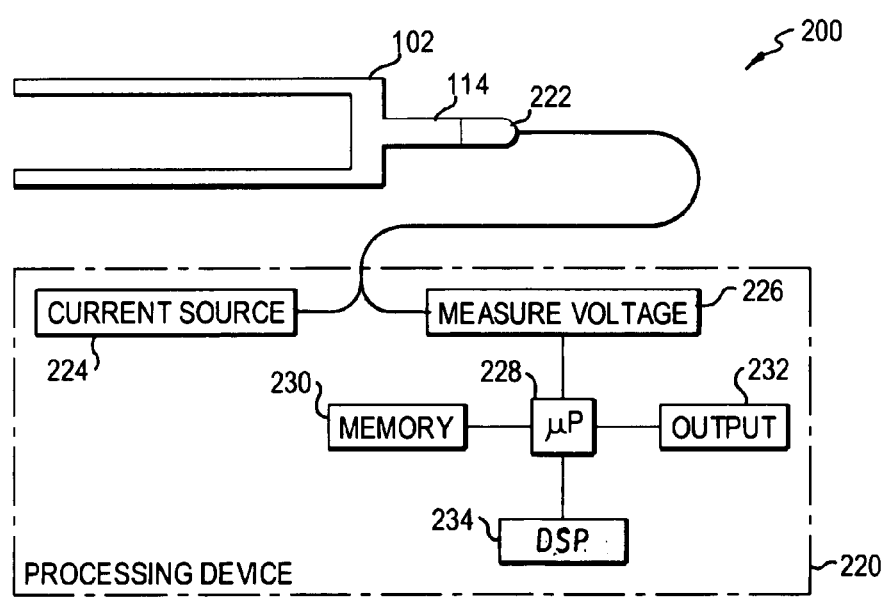

FIG. 3
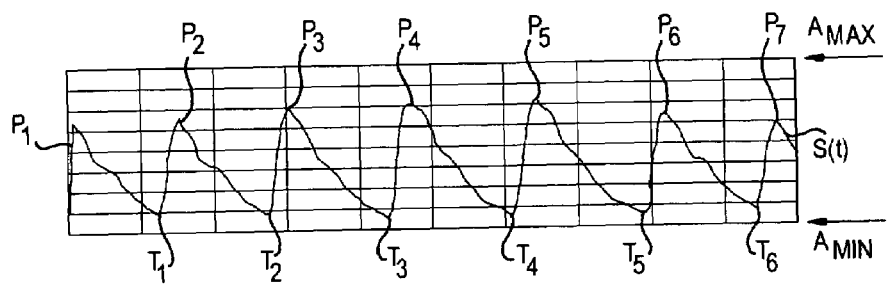
FIG. 4
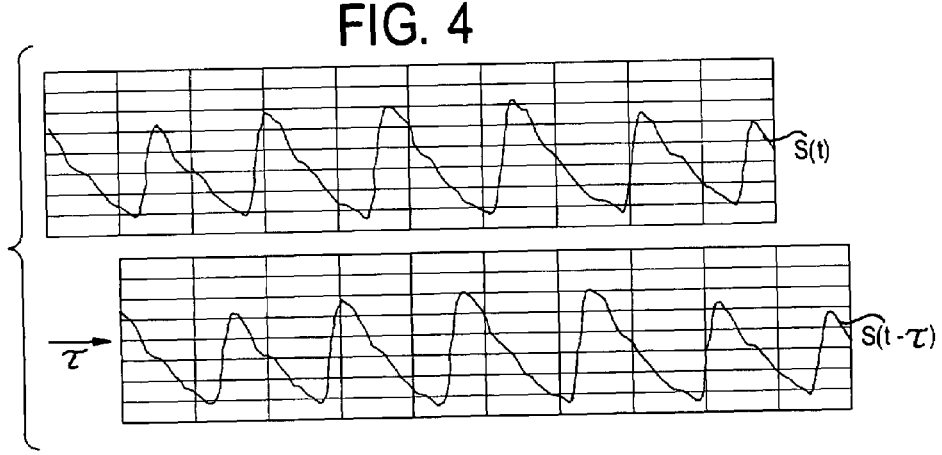
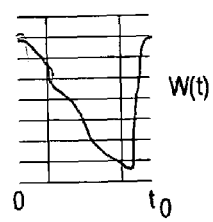
FIG. 5
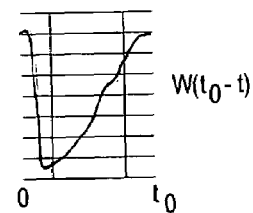
FIG. 6

SIGNAL AVERAGING USING GATING SIGNAL OBTAINED FROM AUTOCORRELATION OF INPUT SIGNALS

FIELD OF THE INVENTION

The present invention is directed to signal averaging to alleviate noise in signals having periodic or almost periodic waveforms, e.g., those taken in pulse volume measurement, and more particularly to such signal averaging in situations in which a gating signal is unavailable.

DESCRIPTION OF RELATED ART

The measurement of peripheral blood flow is important in medicine, since there are many specific diseases in which peripheral blood flow is impaired, e.g., diabetes and atherosclerosis. Also, the peripheral blood flow is altered as the total cardiac output is increased or decreased. Cardiac output is particularly important in patients who are under anesthesia, are in the post-operative state, or are critically ill or unstable. As blood flow from the heart falls, the peripheral blood flow is dramatically reduced to preserve flow to the brain and vital organs.

Blood flow to an extremity can be measured painstakingly and invasively by dissecting out the main blood vessels to the limb (e.g., brachial artery in an arm) and encircling it with an electromagnetic flow probe. That is clearly not a technique suitable for clinical use. It is therefore desired to measure peripheral blood flow non-invasively.

Peripheral impedance (or conductance) plethysmography is a technique for non-invasively measuring peripheral blood flow by measuring peripheral pulse volume, which is the small change in the volume of a limb segment occurring within the cardiac cycle. The technique works by obtaining a raw pulse volume analog signal and applying a selective signal-averaging algorithm to the raw pulse volume signal. The technique is described in U.S. Pat. No. 4,548,211 to Marks.

In the technique as currently practiced, the raw pulse volume analog signal is obtained by measuring the electrical impedance (or conductance) of a limb segment with an electrode such as that of FIG. 1. The electrode 102 is made of a flexible material 104, so that it can be wrapped around the limb segment. The flexible material is configured to define a connecting portion or member 106, which is insulated from direct electrical contact with the patient, and two members 108 for being wrapped around or otherwise applied to the limb segment. Each of the two members 108 contains an outer current electrode 110 paired with an inner voltage electrode 112. An electrical connector 114 allows the outer current electrodes 110 and the inner voltage electrodes 112 to be connected to a source of current and a voltage-measuring device, respectively.

An alternating current on the order of 1 ma amplitude and 40 kHz frequency is applied to the two outer current electrodes, while the inner voltage electrodes are used to measure the voltage resulting from the applied current. The ratio of the amplitude of the voltage waveform to the amplitude of the current waveform is the limb impedance, Z. Measurements of Z over time provide the baseline impedance $Z_0$ of the limb segment and the pulsatile change $\Delta Z$ of the impedance. Knowing the resistivity $\rho$ of the blood and the distance L between the two inner voltage electrodes, the change in volume $\Delta V$ can be calculated as:

$$\Delta V = \rho L^2 \Delta Z / Z_0.$$

The resistivity $\rho$ is either calculated or approximated from the patient's hematocrit. An improvement to the above technique is taught in U.S. patent application Ser. No. 10/392,308, filed Mar. 20, 2003, by Smith et al.

The signal-to-noise ratio in computer-assisted plethysmography can be improved through selective signal averaging. The ECG signal is used as a gating signal. More specifically, the gating signal is based on detection of a QRS complex, which is the series of deflections in an electrocardiogram that represent electrical activity generated by ventricular depolarization prior to contraction of the ventricles. When a QRS complex is detected, a finite time window is opened during which the analog input signal must remain within certain amplitude boundaries. If the analog input signal remains within the defined amplitude boundaries, the waveform is saved for averaging. If not, it is discarded.

However, the above technique has the following drawbacks. To obtain a time reference for the averaging process, an ECG signal must be provided. That requires either additional leads to be applied to the patient or an ECG signal to be provided from another patient monitor. Either of those possibilities increases the number of leads to be applied to the patient and the complexity of the overall equipment to be used.

In an entirely separate field of endeavor, the mathematical technique of autocorrelation has been developed to detect features of data such as periodicity and randomness. Autocorrelation can be considered as the correlation or convolution of a signal with itself, so that the signal is compared to a time-shifted version of itself. Mathematically, the autocorrelation of a signal of finite duration can be expressed as $$R(\tau) = \int_{-\infty}^{\infty} f(t) f(t+\tau) dt.$$

If $f(t)$ is real, the autocorrelation function $R(\tau)$ is real and even. Thus, the above expression is equivalent to $$R(\tau) = \int_{-\infty}^{\infty} f(t) f(t-\tau) dt.$$

The autocorrelation of random noise takes the form of a spike, since random noise is similar only to the non-time-shifted version of itself. On the other hand, the autocorrelation of a periodic signal, in which the time-shifted version goes into and out of phase relative to the non-time-shifted version as the time is shifted, is also periodic. Since a short signal is similar to itself only while it lasts, its autocorrelation drops to zero once the time shift exceeds the lifetime of the signal.

The use of autocorrelation in digital signal processing is well known, as is the design of digital signal processors to carry it out. However, insofar as known, the technique of autocorrelation has not previously been applied to the above-noted limitations of plethysmography.

SUMMARY OF THE INVENTION

It will be readily apparent to those skilled in the art to which the present invention pertains that a need exists in the art to eliminate the need for an ECG signal or other separately supplied gating signal.

It is therefore an object of the present invention to provide a system and method for deriving the gating signal from the input signal itself.

Another object of the invention is to use such a derived gating signal to locate individual waveforms in the input signal.

Still another object of the invention is to use such a derived gating signal to determine time periods in which the waveforms are tested to determine whether they remain in a required amplitude range for averaging.

To achieve the foregoing and other objects, the present invention is directed to a system and method for obtaining a timing reference for the averaging process. It is based upon the autocorrelation (or equivalently, the convolution) signal processing technique. As an illustrative example, consider an analog signal that contains two or more successive plethysmographic waveforms. If the noise content is not excessive, the peak of the autocorrelation function applied to that analog segment will occur at a time interval equal to the distance between the two peaks of the successive plethysmographic waveforms.

In practice, a segment of analog input including more than two waveforms will be acquired and analyzed. The autocorrelation function does not contain a single, precise peak because there is natural variability of the distance between successive plethysmographic waveforms. This is due to cardiac R—R interval variability, which in turn is due, at least in part, to respiration.

In that case, the autocorrelation function provides "first pass" information that determines the range over which the distance between the plethysmographic waveforms varies. Then, a single waveform can be isolated, reversed, and "slid over" the entire waveform segment using the convolution method (that determines how the single waveform should be positioned in time relative to other single plethysmographic waveforms) to facilitate the averaging process. This may be repeated for each single waveform.

An additional benefit is that the amplitude of the correlation function can be used for determining signal-to-noise quality and can provide an additional criterion for waveform acceptance for, or exclusion from, averaging. This technique may be applied to other signal averaging tasks in which a gating signal is either not available or difficult to obtain.

BRIEF DESCRIPTION OF THE DRAWINGS

A preferred embodiment of the present invention is disclosed in detail with reference to the drawings, in which:

FIG. 1 illustrates a plethysmographic electrode according to the prior art;

FIG. 2 is a block diagram of a system on which the preferred embodiment of the method of the invention is implemented;

FIG. 3 depicts an analog plethysmographic signal;

FIG. 4 shows the signal of FIG. 3 compared with a time-shifted version of itself for autocorrelation;

FIG. 5 shows an isolated waveform of the plethysmographic signal;

FIG. 6 shows the isolated waveform of FIG. 5 after time reversal;

DETAILED DESCRIPTION OF THE PREFERRED EMBODIMENTS

Figure 7:
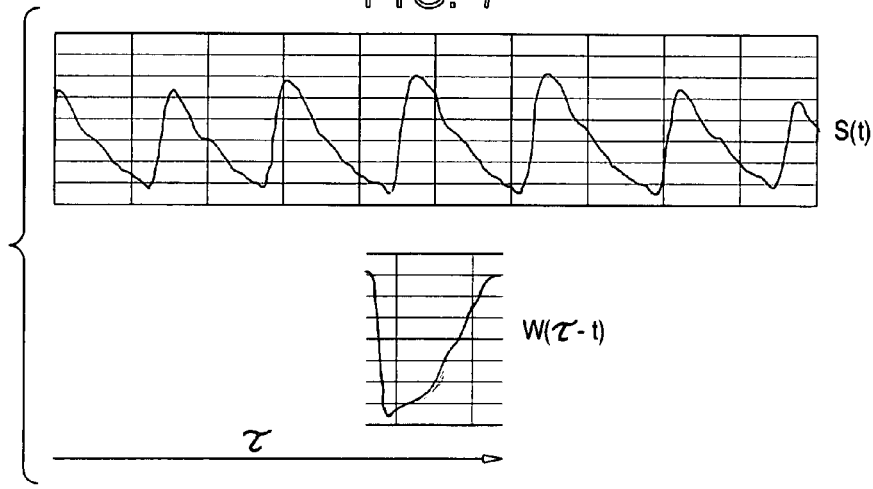
FIG. 7 shows the original signal compared with the reversed isolated waveform for convolution.

A preferred embodiment of the present invention is set forth in detail hereinafter with reference to the drawings.

FIG. 2 shows a block diagram of a device in which the preferred embodiment can be implemented. The device 200 differs from conventional plethysmographic devices and from that of the aforementioned Marks patent and Smith et al application in that, inter alia, it includes a digital signal processor for performing autocorrelation and convolution functions.

The electrode 102 and the processing device 220 are connected by way of electrical connectors 114, 222. In the processing device 220, a current source 224 applies alternating current to the two outer current electrodes to induce a voltage in the two inner voltage electrodes. A voltage-measuring device 226 measures the induced voltage and supplies the measured value to a microprocessor 228 or other suitable processing device. The microprocessor 228 is in communication with a memory 230, which can be a ROM, an EEPROM, or other suitable non-volatile memory, and which stores software routines to perform the operations to be described below. The microprocessor 228 is also in communication with a digital signal processor (DSP) chip 234 that performs DSP functions, such as convolution and autocorrelation. The microprocessor 228 and the DSP chip 234 perform the operations explained below to average the waveforms; then the microprocessor 228 calculates V and outputs the calculated value to any suitable output 232.

Figure 8:
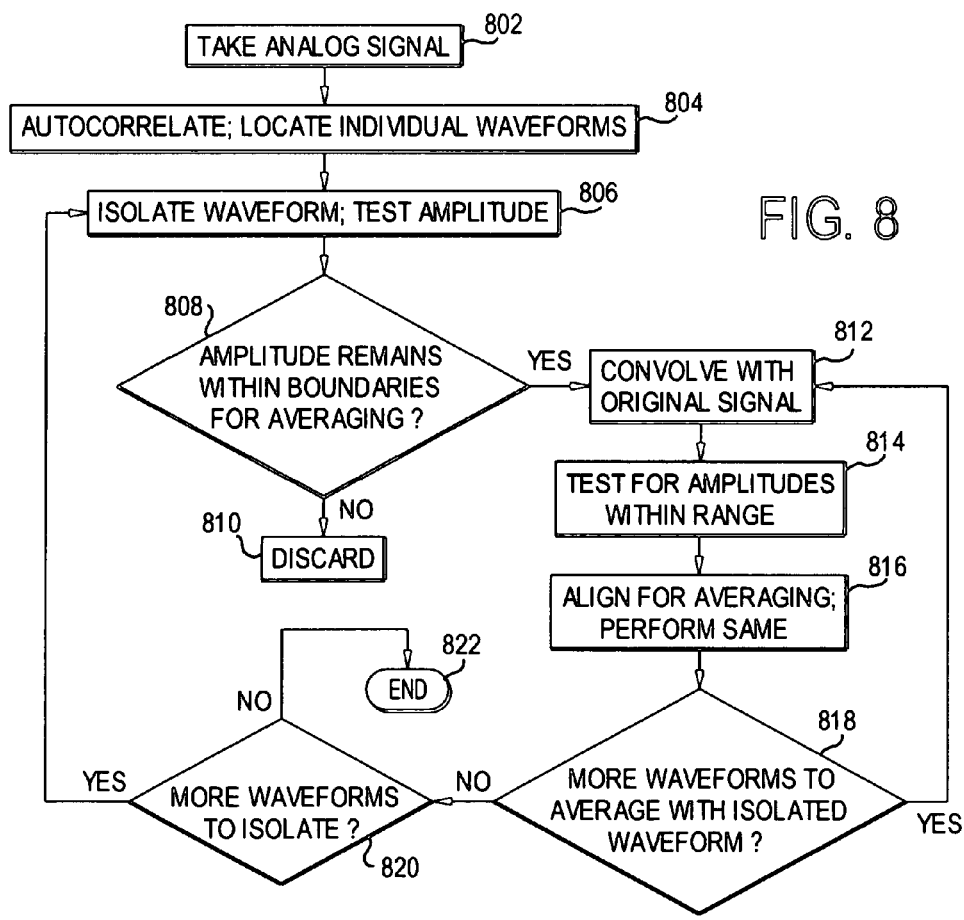
FIG. 8 is a flow chart of the operation of the preferred embodiment.

The device 200 operates in a manner that will now be explained with reference to the waveforms of FIGS. 3–7 and the flow chart of FIG. 8. An analog signal selected by the device (FIG. 8, step 802) has an appearance substantially as shown in FIG. 3. As shown, the analog signal S(t) has a plurality of plethysmographic waveforms defined by peaks $P_1, P_2, P_3, P_4, P_5, P_6, P_7$, and troughs $T_1, T_2, T_3, T_4, T_5, T_6$. If S(t) is autocorrelated with a time-shifted version of itself, S(t-τ), as shown in FIG. 4 and specified in FIG. 8, step 804. Then, if the noise in S(t) is not excessive, the resulting function of r has peaks occurring at a time interval equal to the time interval between successive peaks of S(t). Each waveform to be used in the averaging should be tested to determine whether its amplitude remains in a range between a minimum acceptable amplitude $A_{min}$ and a maximum acceptable amplitude $A_{max}$.

However, in practice, the time interval between successive peaks of S(t) has some variation due to cardiac R—R interval variability, which in turn is due, at least in part, to respiration. Therefore, the autocorrelation function does not contain a single, precise peak.

To overcome that difficulty, the autocorrelation function is not taken as the final answer, but instead provides first-pass information about the range over which the distance between the successive peaks of S(t) varies. By use of that first-pass information, a single waveform W(t), t=0 through $t_0$, can be isolated, as shown in FIG. 5, as specified in FIG. 8, step 806, and as tested in FIG. 8, steps 806 and 808, to determine whether its amplitude remains in the boundaries required for averaging; if not, it is discarded in FIG. 8, step 810. That waveform, if not discarded, can then be reversed to form $W(t_0-t)$, as shown in FIG. 6. The reversed waveform can be convolved with S(t), or "slid over" S(t), as shown in FIG. 7 and specified in FIG. 8, step 812. The convolution of two waveforms shown in FIG. 7 can be mathematically expressed as $$C(\tau)=\int S(t)W(\tau-t)dt.$$

The peaks (local maxima) of the convolution as a function of τ give the best matches between the peak of W(t) and the peaks of the other single plethysmographic waveforms included in S(t). Thus, the sliding or convolution can be used to determine the time window during which the input signal must remain within the amplitude boundaries mentioned above, as determined in FIG. 8, step 814. The sliding or convolution can also be used to determine how the waveform W(t) should be positioned in time relative to the other single plethysmographic waveforms for the averaging operation, as specified in FIG. 8, step 816. The isolated waveform can be matched and averaged with multiple other waveforms in the signal, as specified in FIG. 8, step 818. Each single waveform in S(t) can be isolated, so that the sliding can be repeated for each single waveform, as specified in FIG. 8, step 820. The matching and averaging process ends in step 822, whereupon an averaged signal is available for calculating V.

The present invention is not limited to plethysmography, but instead can be applied to any signal averaging task in which it is difficult or impossible to obtain a gating signal. In particular, the present invention can be used with regard to any signal that is periodic or almost periodic and that has considerable noise. One example is analysis of a waveform indicating shaking in a device such an automobile. Since the same problems with signal averaging may arise with such a waveform as those noted above with a plethysmographic waveform, the present invention is applicable in such situations as well. Of course, those skilled in the art who have reviewed the present disclosure will readily appreciate the other situations in which the present invention can be used.

While a preferred embodiment of the present invention has been set forth above, those skilled in the art who have reviewed the present disclosure will readily appreciate that other embodiments can be realized within the scope of the invention. For example, as explained above, the present invention can be applied to other signal averaging tasks in which it is difficult or impossible to obtain a gating signal. Also, disclosures of specific waveforms are illustrative rather than limiting. Therefore, the present invention should be construed as limited only by the appended claims.

We claim:

1. A method for performing pulse volume measurement on a patient, the method comprising:
   (a) taking a plethysmographic signal from the patient, the plethysmographic signal comprising a plurality of plethysmographic waveforms;
   (b) performing an autocorrelation on the plethysmographic signal to determine locations of the individual plethysmographic waveforms;
   (c) isolating one of the plethysmographic waveforms in accordance with the autocorrelation;
   (d) convolving the isolated plethysmographic waveform with the plethysmographic signal to align the isolated plethysmographic waveform with the plethysmographic signal;
   (e) performing signal averaging between the isolated plethysmographic waveform and the plethysmographic signal as aligned in step (d) to provide an averaged signal; and
   (f) performing the pulse volume measurement in accordance with the averaged signal.

2. The method of claim 1, wherein step (c) comprises determining whether the isolated plethysmographic waveform has an amplitude which remains in a predetermined range.

3. The method of claim 2, wherein step (d) comprises determining a time window in which the plethysmographic signal is tested to determine whether the plethysmographic signal has an amplitude which remains in the predetermined range during the time window.

4. The method of claim 3, wherein steps (d) and (e) are performed for a plurality of plethysmographic waveforms in the plethysmographic signal.

5. The method of claim 4, wherein step (c) is performed for a plurality of plethysmographic waveforms in the plethysmographic signal to provide a plurality of isolated plethysmographic waveforms, and wherein steps (d) and (e) are performed for the plurality of isolated plethysmographic waveforms.

6. A method for averaging a signal which comprises a plurality of individual waveforms in sequence, the method comprising:
   (a) performing an autocorrelation on the signal to determine locations of the individual waveforms in the signal;
   (b) isolating one of the waveforms in accordance with the autocorrelation;
   (c) time-shifting the isolated waveform to align the isolated waveform with another waveform in the signal; and
   (d) averaging the isolated waveform and the other waveform.

7. The method of claim 6, wherein step (c) comprises performing a convolution of the isolated waveform with the signal to determine an optimal alignment between the isolated waveform and the other waveform.

8. The method of claim 7, wherein step (c) further comprises using the convolution to determine a time window containing the other waveform and determining whether, during the time window, an amplitude of the other waveform remains within a predetermined range.

9. The method of claim 8, wherein steps (c) and (d) are performed a plurality of times for a plurality of other waveforms in the signal.

10. The method of claim 9, wherein step (b) is performed a plurality of times to provide a plurality of isolated waveforms, and wherein steps (c) and (d) are performed for each of the isolated waveforms.

11. The method of claim 6, wherein step (b) comprises testing the isolated waveform to determine whether the isolated waveform has an amplitude which remains in a predetermined range.

12. The method of claim 6, wherein the signal is a plethysmographic signal.

13. The method of claim 12, wherein the signal is taken in a circumstance in which a separate ECG signal is not available.

14. The method of claim 6, wherein the signal is periodic.

15. The method of claim 6, wherein the signal is approximately periodic.

16. A system for averaging a signal which comprises a plurality of individual waveforms in sequence, the system comprising:
   an input for receiving the signal; and
   circuitry, in communication with the input, for:
   (a) performing an autocorrelation on the signal to determine locations of the individual waveforms in the signal;

(b) isolating one of the waveforms in accordance with the autocorrelation;
(c) time-shifting the isolated waveform to align the isolated waveform with another waveform in the signal; and
(d) averaging the isolated waveform and the other waveform.

17. The system of claim 16, wherein the circuitry performs step (c) by performing a convolution of the isolated waveform with the signal to determine an optimal alignment between the isolated waveform and the other waveform.

18. The system of claim 17, wherein the circuitry performs step (c) further by using the convolution to determine a time window containing the other waveform and determining whether, during the time window, an amplitude of the other waveform remains within a predetermined range.

19. The system of claim 18, wherein the circuitry performs steps (c) and (d) a plurality of times for a plurality of other waveforms in the signal.

20. The system of claim 19, wherein the circuitry performs step (b) a plurality of times to provide a plurality of isolated waveforms, and wherein steps (c) and (d) are performed for each of the isolated waveforms.

21. The system of claim 16, wherein the circuitry performs step (b) by testing the isolated waveform to determine whether the isolated waveform has an amplitude which remains in a predetermined range.

22. The system of claim 14, wherein the circuitry comprises a digital signal processor.

* * * * *